(12) United States Patent
Backe (10) Patent No.: US 11,641,542 B2
(45) Date of Patent: May 2, 2023

(54) EARPIECE WITH INTERNAL UV CLEANING

(71) Applicant: Michael Backe, Valdosta, GA (US)

(72) Inventor: Michael Backe, Valdosta, GA (US)

( * ) Notice: Subject to any disclaimer, the term of this patent is extended or adjusted under 35 U.S.C. 154(b) by 53 days.

(21) Appl. No.: 17/327,917

(22) Filed: May 24, 2021

(65) Prior Publication Data

US 2022/0150617 A1 May 12, 2022

Related U.S. Application Data

(60) Provisional application No. 63/112,681, filed on Nov. 12, 2020.

(51) Int. Cl.
*H04R 1/10* (2006.01)
*A61L 2/10* (2006.01)
*A61L 2/26* (2006.01)

(52) U.S. Cl.
CPC .............. *H04R 1/1091* (2013.01); *A61L 2/10* (2013.01); *A61L 2/26* (2013.01); *H04R 1/1016* (2013.01); *H04R 1/1025* (2013.01); *H04R 1/1041* (2013.01); *H04R 1/1075* (2013.01); *A61L 2202/11* (2013.01); *A61L 2202/16* (2013.01); *H04R 2420/07* (2013.01)

(58) Field of Classification Search
CPC .. H04R 1/1091; H04R 1/1016; H04R 1/1025; H04R 1/1041; H04R 1/1075; H04R 2420/07; A61L 2/10; A61L 2/26; A61L 2202/11; A61L 2202/16
USPC ......................................................... 381/74
See application file for complete search history.

(56) References Cited

U.S. PATENT DOCUMENTS

2021/0039141 A1* 2/2021 Behrbom ............. H04R 1/1016
2022/0086547 A1* 3/2022 Oh ........................ H04R 1/028

* cited by examiner

*Primary Examiner* — Paul Kim
(74) *Attorney, Agent, or Firm* — Larson & Larson; Justin P. Miller; Frank Liebenow (57) ABSTRACT

The earpiece with internal UV cleaning source includes one or more internal UV light sources, specifically emitting UVC light. The UVC light is emitted during charging of the earbud, thus conserving battery power by only emitting during periods of ample power availability. In a preferred embodiment, the UV light is emitted behind the speaker, passing through and bouncing around the clear speaker mounting bracket, or through holes in the housing/frame bracket. The result is that all internal sections of the earpiece that could harbor bacteria or viruses are exposed to the UV light.

16 Claims, 8 Drawing Sheets

EARPIECE WITH INTERNAL UV CLEANING

PRIORITY CLAIM

This application claims priority to U.S. Pat. App. No. 63/112,681, filed Nov. 12, 2020, titled Earpiece with internal UV cleaning.

FIELD

This invention relates to the field of in-ear audio devices and more particularly to an earpiece with internal UV sterilization.

BACKGROUND

As electronics have progressed, headphones have become progressively smaller and more feature-packed.

Headphones that originally used a headband, and sat against the outer ear, now sit tucked away inside the ear, often barely visible. Within the compact housing is the speaker, partially sitting inside the ear canal.

While the compact profile is practical and visually appealing, natural ventilation and the associated drying and cleaning are lost. The housing no longer sits against the dry, ventilated outer ear, but rather within the moist ear canal. The housing or earbud itself further seals off the ear canal, excluding outside sounds but also preventing ventilation.

What is needed is a device that can compensate for the lack of airflow by disinfecting headphones placed in or near the ear.

SUMMARY

The earpiece with internal UV cleaning source includes one or more internal UV light sources, specifically emitting UVC light.

The UVC light is emitted during charging of the earbud, thus conserving battery power by only emitting during periods of ample power availability.

In one embodiment, the internal UVC light does not electrically connect to the internal battery, but is powered by a separate circuit.

Thus, the UVC light cannot consume power from the internal battery, but can only consume power when the device is placed in a charger.

In other embodiments, the UVC light is separated from the internal battery by a switch, permitting the UVC light to be activated while charging, but without the requirement of a separate circuit.

The parts of the device include:
An earpiece body;
One or more internal UV emitters;
One or more speakers, preferably with clear housing/frame to allow UV light to pass through and around speaker, or the housing/frame including one or more holes to allow light to pass through;
An optional internal reflective coating to aid in transmission of UV light;
An optional UV filter at the outlet, blocking UV light from exiting the earpiece body; and
Associated earpiece/earbud electronics, including power source, charging circuit, audio processing circuitry, one or more wireless antennas, accelerometer, orientation sensor, and related electronics.

In a preferred embodiment, the UV light is emitted behind the speaker, passing through and bouncing around the clear speaker mounting bracket. Alternatively, the housing/frame includes one or more holes to allow light to pass through. The result is that all internal sections of the earpiece that could harbor bacteria or viruses are exposed to the UV light.

To expand on the discussion of UV light, the ideal UV light spectrum for destruction of bacteria and viruses is shortwave UV. Specifically, UVC light is ultraviolet light with a wavelength of between 100 and 280 nanometers.

The exact wavelength emitted by the bulb varies depending on the type of light source used. For example, a fluorescent lamp tube with no phosphor coating primarily emits ultraviolet light at 253.7 nm and 185 nm.

An LED UV light source primarily emits at wavelengths of 214 nm, 265 nm, and 273 nm, with lesser emissions at other frequencies.

An LED is preferred given the low power consumption and minimal heat generation, but other sources of UVC light may be substituted.

While the disclosure focuses on an earpiece used for audio, such as earbuds used for exercising, the use of UVC light for internal sterilization may be applied to many devices including hearing aids, earplugs, in-ear monitors, and so forth.

BRIEF DESCRIPTION OF THE DRAWINGS

The invention can be best understood by those having ordinary skill in the art by reference to the following detailed description when considered in conjunction with the accompanying drawings in which.

DETAILED DESCRIPTION

Reference will now be made in detail to the presently preferred embodiments of the invention, examples of which are illustrated in the accompanying drawings. Throughout the following detailed description, the same reference numerals refer to the same elements in all figures.

Figure 1:
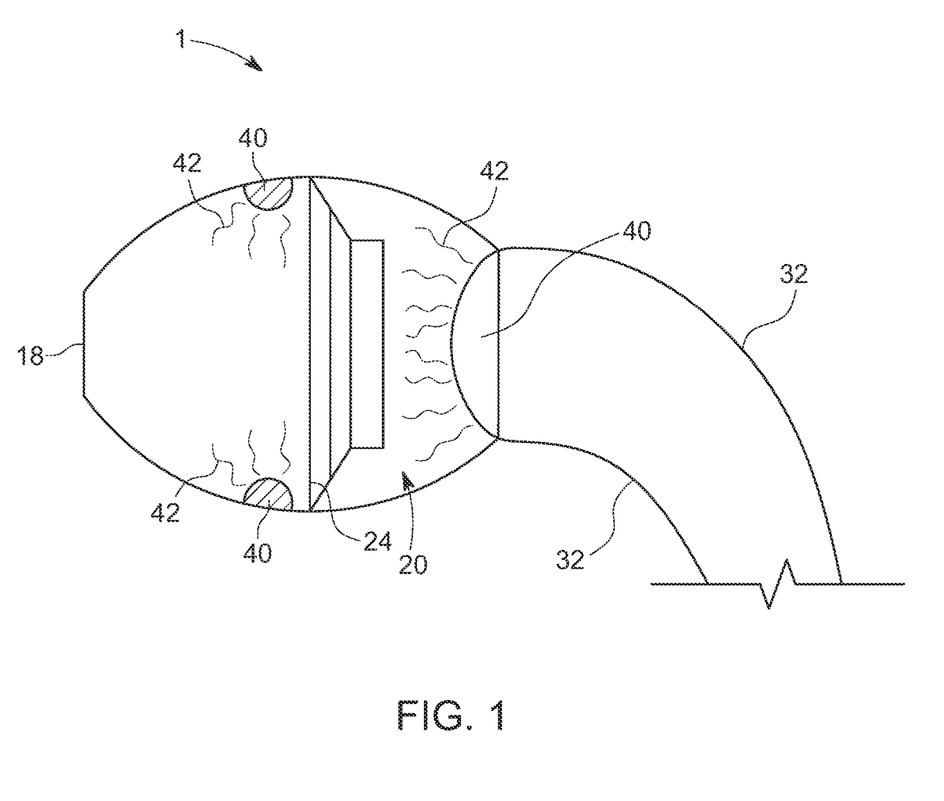
FIG. 1 illustrates a first schematic view of the earpiece with internal UV cleaning.

Referring to FIG. 1, a first schematic view of the earpiece with internal UV cleaning is shown.

The earpiece with internal UV cleaning 1 is shown with speaker 20 held within a speaker frame 24. Sound exits the earpiece with internal UV cleaning 1 via the audio passageway 18.

The audio signal is carried using cables 32.

Multiple UV light sources 40 emit UV light 42, cleaning the inside of the earpiece with internal UV cleaning 1.

Figure 2:
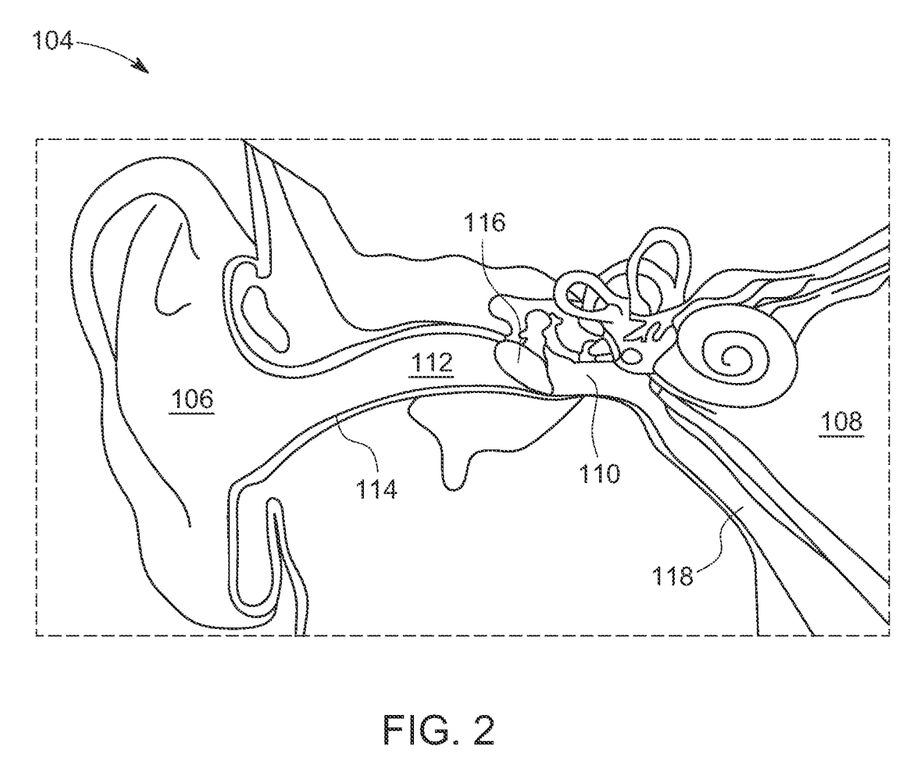
FIG. 2 illustrates a sectional view of a typical human ear.

Referring to FIG. 2, a Sectional View of a Typical Human Ear is Shown.

The ear 104 includes an outer ear 106, inner ear 108, and middle ear 110. The ear canal 112, along the ear canal wall 114, carries sound to the ear drum 116.

The Eustachian tube 118 allows for equalization of pressure between the middle ear 110 and the nasal cavities.

Figure 3A:
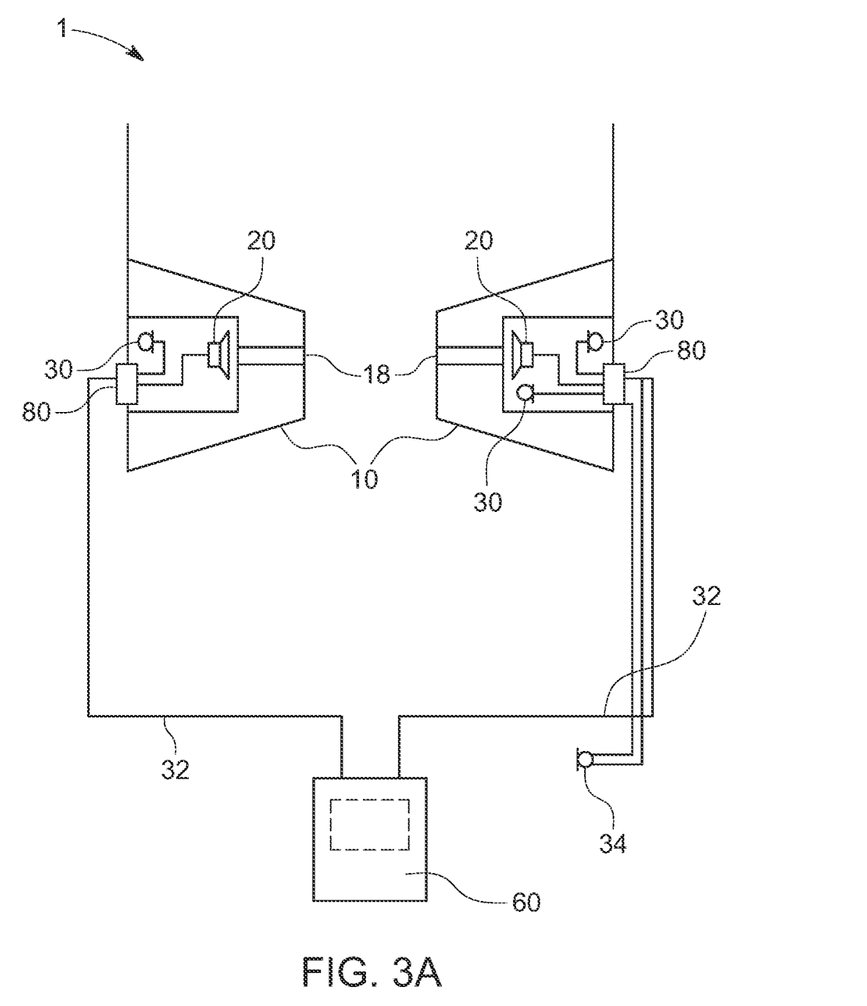
FIG. 3A illustrates a second schematic view of the earpiece with internal UV cleaning.
Figure 3B:
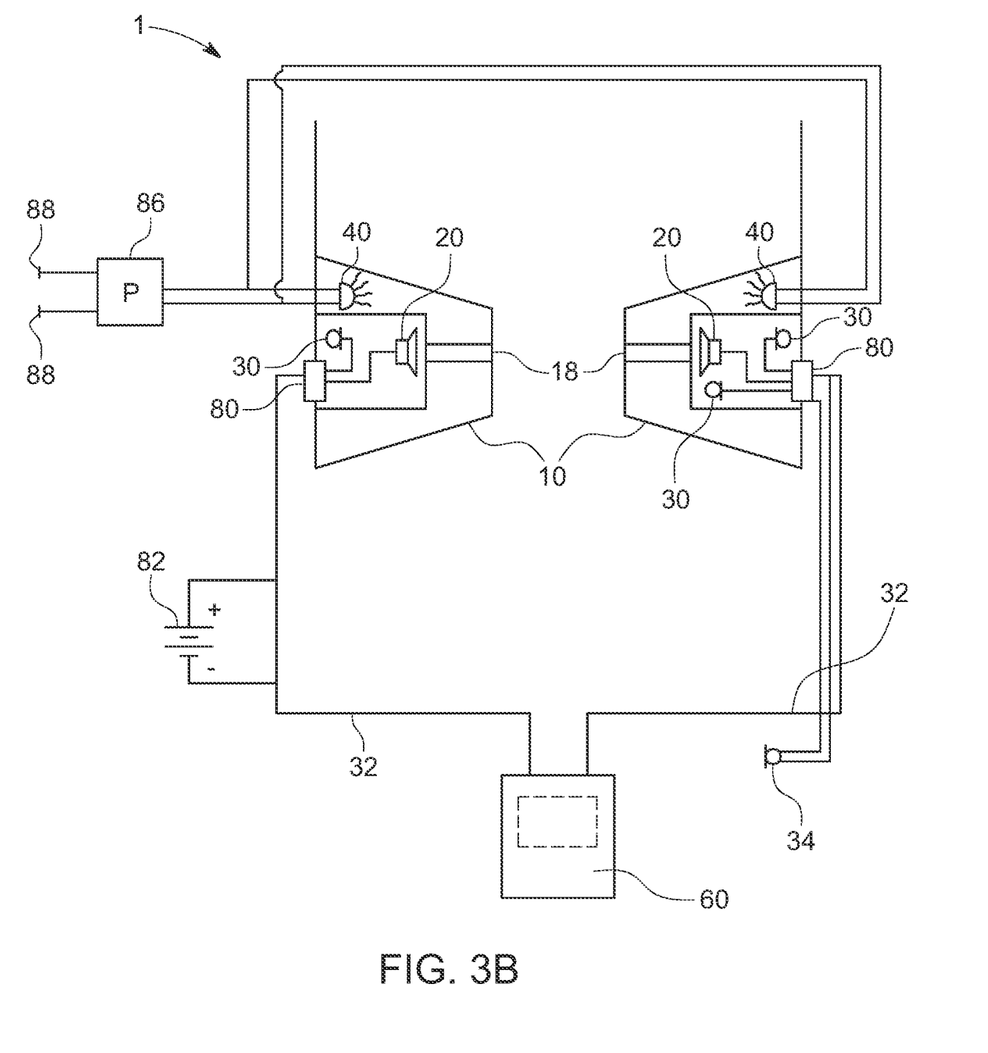
FIG. 3B illustrates a third schematic view of the earpiece with internal UV cleaning.

Referring to FIGS. 3A and 3B, second and third schematic views of the earpiece with internal UV cleaning are shown.

The earpiece with internal UV cleaning 1 is shown in a second configuration, with speaker 20 communicating with audio passageway 18. A microphone 30 allows the user to use the earpiece with internal UV cleaning 1 for phone calls, signals passing through cables 32 to a controller 34.

Circuitry 80 processes data, such as volume inputs or noise reduction.

The audio source 60 may be a phone, mp3 player, or other device.

In the embodiment shown in FIG. 3B, power for the audio components of the earpiece with internal UV cleaning 1 is provided by the internal battery 82. The UV light sources 40 are powered separately, by an external power source 86, connected via charger contacts 88, resulting in an electrical circuit that is wholly separate from the internal battery 82.

Figure 4:
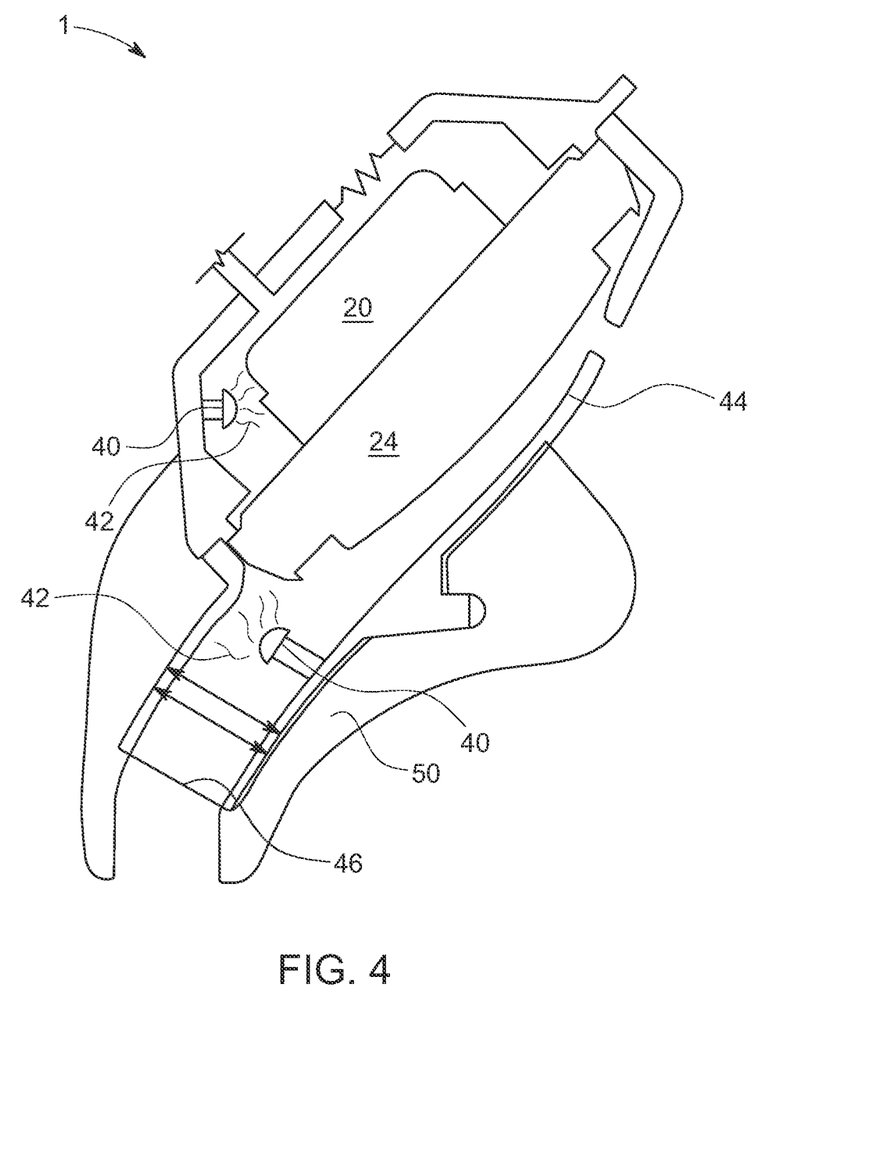
FIG. 4 illustrates a fourth schematic view of the earpiece with internal UV cleaning.

Referring to FIG. 4, a third schematic view of the earpiece with internal UV cleaning is shown.

This embodiment of the earpiece with internal UV cleaning 1 includes a speaker 20 with speaker frame 24, the speaker frame 24 preferably constructed of a material that is transparent to UV light.

One or more UV light sources 40 are shown, emitting UV light 42. An optional internal reflective surface 44 allows the UV light 42 to spread around the interior of the earpiece with internal UV cleaning 1.

Also shown is an optional UV filter 46 at the outlet, blocking UV light 42 from exiting the earpiece with internal UV cleaning 1.

Figure 5:
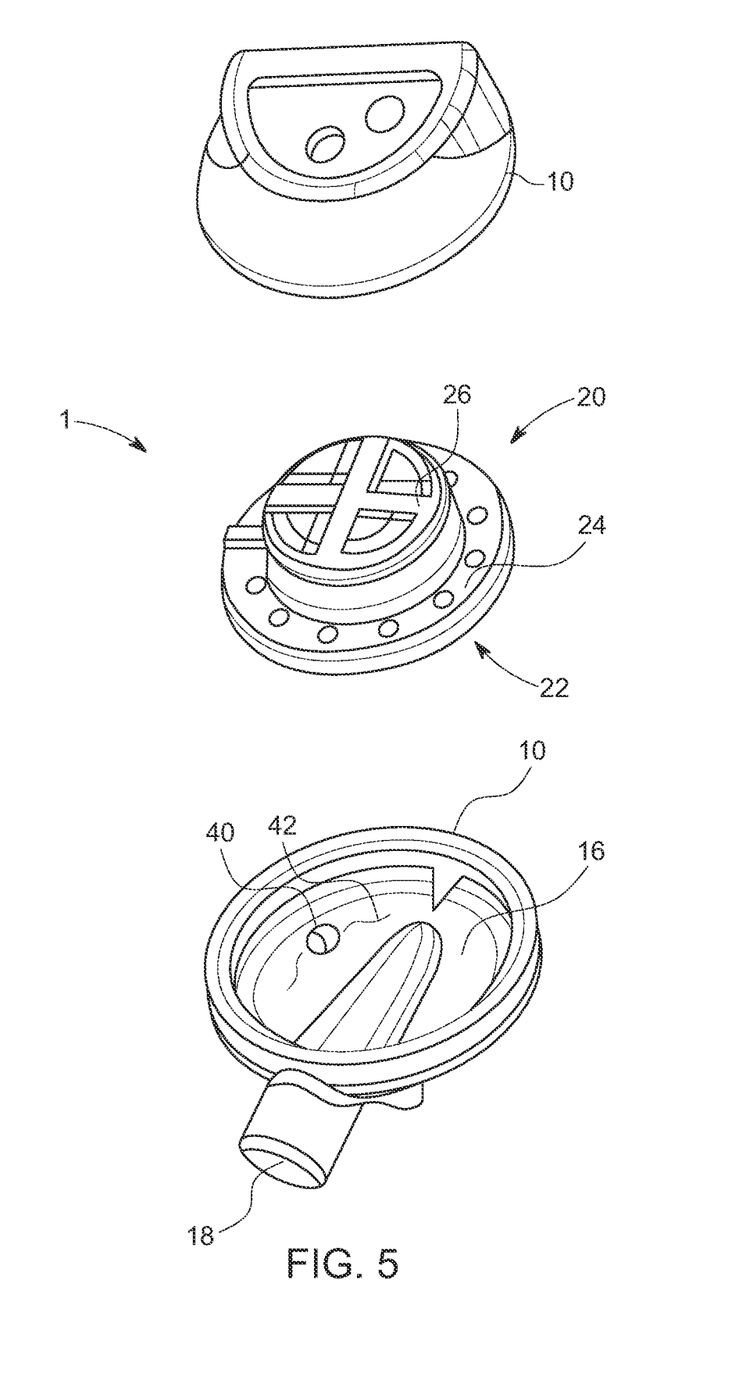
FIG. 5 illustrates an exploded view of the earpiece with internal UV cleaning.

Referring to FIG. 5, an exploded view of the earpiece with internal UV cleaning is shown.

The earpiece with internal UV cleaning 1 includes a body/housing 10 that separates into two or more pieces.

When assembled, a cavity 16 holds the speaker 20, speaker cone 22 (under the speaker 20 in this figure), speaker frame 24, and speaker magnets and coil 26.

Also shown is UV light source 40 emitting UV light 42.

Figure 6:
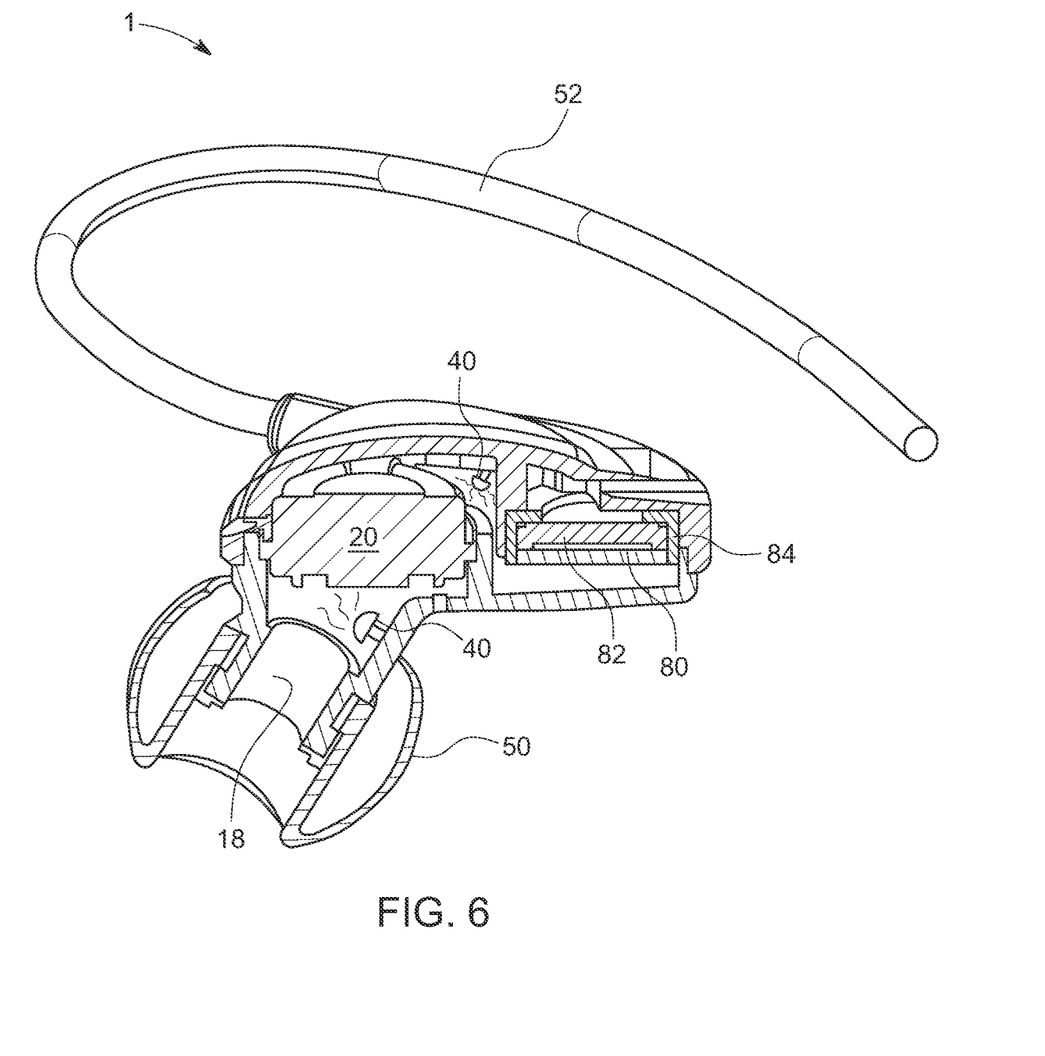
FIG. 6 illustrates a sectional view of the earpiece with internal UV cleaning.
Figure 7:
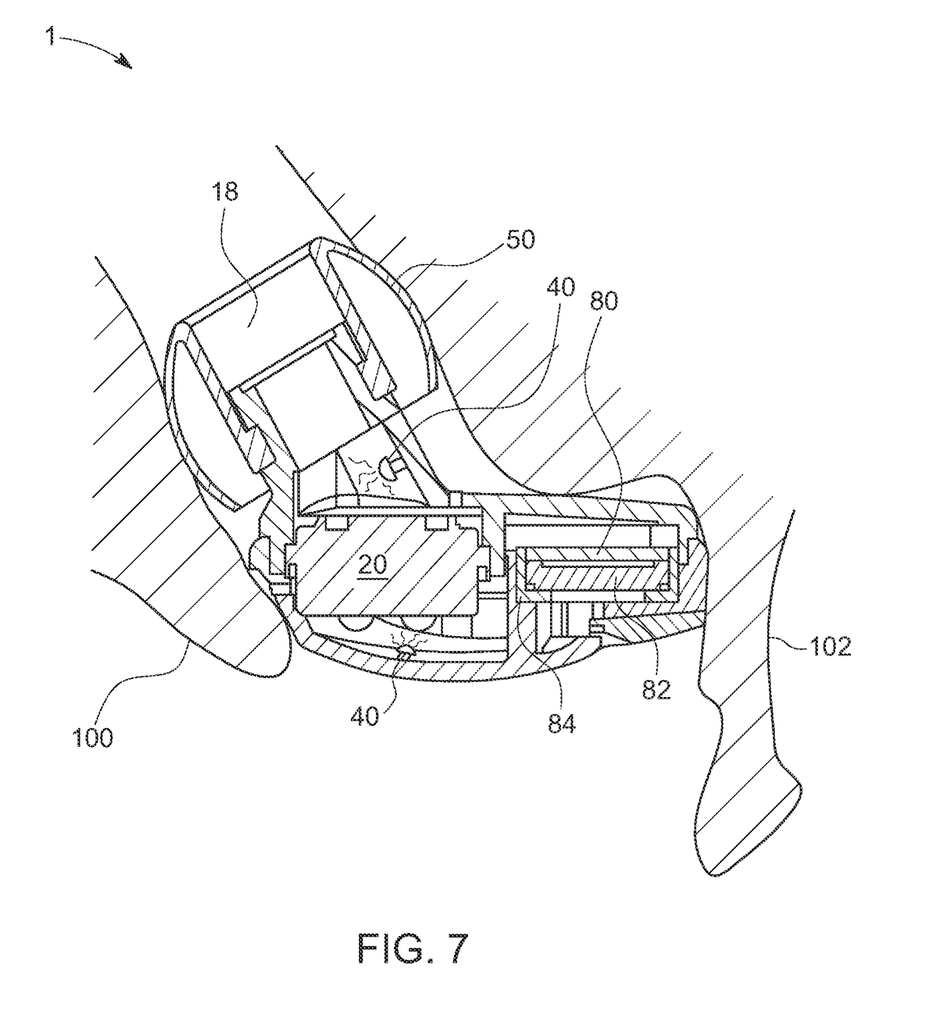
FIG. 7 illustrates a sectional view, after placement in a human ear, of the earpiece with internal UV cleaning.

Referring to FIGS. 6 and 7, a sectional view of the earpiece with internal UV cleaning is shown, both outside the ear and after placement into a human ear.

The earpiece with internal UV cleaning 1 is shown with a speaker 20, allowing sound to exit through audio passageway 18.

A silicone tip 50 and earloop 52 help the earpiece with internal UV cleaning 1 to sit within and around an ear.

When in place, the silicone tip 50 sits within the ear, the speaker 20 toward the front of head 100 and the circuitry 80, the internal battery 82, and Bluetooth transceiver 84 located in a space closer to the back of head 102.

Equivalent elements can be substituted for the ones set forth above such that they perform in substantially the same manner in substantially the same way for achieving substantially the same result.

It is believed that the system and method as described and many of its attendant advantages will be understood by the foregoing description. It is also believed that it will be apparent that various changes may be made in the form, construction, and arrangement of the components thereof without departing from the scope and spirit of the invention or without sacrificing all of its material advantages. The form herein before described being merely exemplary and explanatory embodiment thereof. It is the intention of the following claims to encompass and include such changes.

What is claimed is:

1. An in-ear audio device with internal cleaning comprising:
   a housing;
   an internal battery;
     the internal battery within the housing;
   a speaker;
     the speaker within the housing;
   a UV light source within the housing, the UV light source creating UV light;
     the UV light source activating when the in-ear audio device is placed into a charger;
     the UV light source being electrically separate from the internal battery, thus preventing the UV light from consuming energy from the internal battery;
     the UV light source placed behind the speaker;
   a clear speaker mounting bracket;
     the clear speaker mounting bracket support the speaker with respect to the housing;
     the clear speaker mounting bracket allowing the UV light from the UV light source behind the speaker to pass around the speaker, thus sterilizing the housing directly behind the speaker;
   whereby the UV light is only activated when the in-ear audio device is connected to the charger.

2. The in-ear audio device with internal cleaning of claim 1, further comprising:
   an audio passageway;
     the audio passageway allowing vibration from the speaker to exit the housing;
     the speaker located between the UV light source and the audio passageway;
     whereby the UV light source sanitizes an inside of the housing.

3. The in-ear audio device with internal cleaning of claim 1, further comprising:
   an internal reflective surface;
   whereby the internal reflective surface allows the UV light to reflect inside the housing, thus improving sterilization.

4. The in-ear audio device with internal cleaning of claim 1, further comprising:
   internal electronics, including a Bluetooth receiver;
   whereby the in-ear audio device can wirelessly connect to a cellphone or other source of audio signal.

5. The in-ear audio device with internal cleaning of claim 1, further comprising:
   a UV light filter at an exit to the housing;
   whereby the UV light filter prevents the UV light from exiting the in-ear audio device.

6. The in-ear audio device with internal cleaning of claim 1, whereby:
   the UV light source is a first UV light source and a second UV light source;
     the first UV light source located behind the speaker;
     the second UV light source located in front of the speaker;
   whereby the first UV light source and the second UV light source sterilize around the speaker.

7. An in-ear audio device with internal cleaning that does not consume battery power, the in-ear audio device comprising:
   a housing;
   a speaker within the housing;
   an internal battery within the housing;

a light source that emits ultraviolet light with a wavelength of between 100 and 280 nanometers;
the light source only able to emit ultraviolet light when the in-ear audio device is connected to an external charger;
an internal reflective surface;
whereby the internal reflective surface allows the ultraviolet light with a wavelength of between 100 and 280 nanometers to reflect inside the housing, thus improving sterilization;
a clear speaker mounting bracket;
the clear speaker mounting bracket support the speaker with respect to the housing;
the clear speaker mounting bracket allowing the ultraviolet light with a wavelength of between 100 and 280 nanometers to pass around the speaker, thus sterilizing the housing directly in front of the speaker and directly behind the speaker;
whereby the ultraviolet light only emits light when the in-ear audio device is connected to an external charger, thus avoiding consuming power from the internal battery.

8. The in-ear audio device with internal cleaning that does not consume battery power of claim 7, further comprising:
an audio passageway;
the audio passageway allowing vibration from the speaker to exit the housing;
the speaker located between the light source and the audio passageway;
whereby the ultraviolet light with a wavelength of between 100 and 280 nanometers sterilizes an inside of the housing.

9. The in-ear audio device with internal cleaning that does not consume battery power of claim 7, further comprising:
internal electronics, including a Bluetooth receiver;
whereby the in-ear audio device can wirelessly connect to a cellphone or other source of audio signal.

10. The in-ear audio device with internal cleaning that does not consume battery power of claim 7, further comprising:
a UV light filter at an exit to the housing;
whereby the UV light filter prevents ultraviolet light with a wavelength of between 100 and 280 nanometers from exiting the in-ear audio device.

11. The in-ear audio device with internal cleaning of claim 7, whereby:
the light source is a first light source and a second light source;
the first light source located behind the speaker;
the second light source located in front of the speaker;
whereby the first light source and the second light source sterilize around the speaker.

12. An audio earpiece with internal sterilization comprising:
a housing;
a speaker within the housing;
a battery within the housing;
one or more sources of UVC light;
the one or more sources of UVC light within the housing;
at least one of the one or more sources of UVC light placed behind the speaker;
a clear speaker mounting bracket;
the clear speaker mounting bracket support the speaker with respect to the housing;
the clear speaker mounting bracket allowing the UVC light to pass around the speaker, thus sterilizing the housing directly behind the speaker;
an internal reflective surface;
whereby the internal reflective surface allows the UVC light to reflect inside the housing, thus improving sterilization;
whereby the one or more sources of UVC light are activated when the audio earpiece is charged, the UVC light sterilizing an inside of the audio earpiece.

13. The audio earpiece of claim 12, further comprising:
an audio passageway;
the audio passageway allowing vibration from the speaker to exit the housing;
the speaker located between the one or more sources of UVC light and the audio passageway;
whereby the one or more sources of UVC light sanitize the housing and components within the housing.

14. The audio earpiece of claim 12, further comprising:
internal electronics, including a Bluetooth receiver;
whereby the audio earpiece can wirelessly connect to a cellphone or other source of audio signal.

15. The audio earpiece of claim 12, further comprising:
a UV light filter at an exit to the housing;
whereby the UV light filter prevents the UVC light from exiting the audio earpiece.

16. The audio earpiece of claim 12, whereby:
the one or more sources of light is a first UV light source and a second UV light source;
the first UV light source located behind the speaker;
the second UV light source located in front of the speaker;
whereby the first UV light source and the second UV light source sterilize around the speaker.

* * * * *